United States Patent
Hidaka et al.

(10) Patent No.: US 10,883,952 B2
(45) Date of Patent: *Jan. 5, 2021

(54) METHOD FOR CALCULATING DIELECTRIC CONSTANT OF PARTICLE-DISPERSED COMPOSITE MATERIALS AND METHOD FOR EVALUATING DISPERSIBILITY

(71) Applicant: SHIRAISHI KOGYO KAISHA, LTD., Osaka (JP)

(72) Inventors: Jusuke Hidaka, Amagasaki (JP); Kizuku Kushimoto, Sendai (JP)

(73) Assignee: SHIRAISHI KOGYO KAISHA, LTD., Osaka (JP)

( * ) Notice: Subject to any disclaimer, the term of this patent is extended or adjusted under 35 U.S.C. 154(b) by 307 days.

This patent is subject to a terminal disclaimer.

(21) Appl. No.: 15/766,141

(22) PCT Filed: Oct. 12, 2016

(86) PCT No.: PCT/JP2016/080229
§ 371 (c)(1),
(2) Date: Apr. 5, 2018

(87) PCT Pub. No.: WO2017/065165
PCT Pub. Date: Apr. 20, 2017

(65) Prior Publication Data
US 2018/0292343 A1 Oct. 11, 2018

(30) Foreign Application Priority Data
Oct. 15, 2015 (JP) .................. 2015-203594

(51) Int. Cl.
*G01N 27/22* (2006.01)
*G01R 27/26* (2006.01)
*G01N 33/00* (2006.01)

(52) U.S. Cl.
CPC ....... *G01N 27/221* (2013.01); *G01R 27/2605* (2013.01); *G01R 27/2617* (2013.01); *G01N 2033/0091* (2013.01)

(58) Field of Classification Search
CPC .................. G01N 27/221; G01R 27/2617
See application file for complete search history.

(56) References Cited

U.S. PATENT DOCUMENTS 4,301,401 A 11/1981 Roof et al.
5,451,882 A 9/1995 Wakino et al.
(Continued)

FOREIGN PATENT DOCUMENTS

CN 201060237 Y 5/2008
CN 102818937 A 12/2012
(Continued)

OTHER PUBLICATIONS

Chinese Office Action dated Nov. 1, 2019, issued in counterpart Chinese Patent Application No. 201680060032.8. (6 pages).
(Continued)

*Primary Examiner* — Noam Reisner
(74) *Attorney, Agent, or Firm* — Westerman, Hattori, Daniels & Adrian, LLP

(57) ABSTRACT

A method for calculating the dielectric constant of particle-dispersed composite materials that enables an easy evaluation of dispersibility. The composite material is assumed as a cell combination 10 in which unit cells 1 having a length a are combined together in an x-axis, a y-axis, and a z-axis direction and which has a length l in the x-axis direction, a length m in the y-axis direction, and a length n in the z-axis direction, the cell combination 10 is created in which a particle element or a medium element is assigned to each of the unit cells 1 Layers have a thickness d in the z-axis
(Continued)

direction are combined and layered in the z-axis direction and assigning a capacitance $C_{Layer,h}$ of each of the layers represented by Formula 1 below to Formula 2 to determine a relative dielectric constant $\varepsilon_{Total}$.

$$C_{Layer,h} = \left\{ \sum_{j=1}^{\lfloor m/a \rfloor} \sum_{i=1}^{\lfloor l/a \rfloor} \left( \sum_{k=1}^{\lfloor d/a \rfloor} \frac{1}{\varepsilon_{ijk} \varepsilon_0 a} \right)^{-1} \right\}^{-1} \quad \text{Formula 1}$$

$\varepsilon 0$: dielectric constant of vacuum (F/m)

$$\varepsilon_{Total} = \frac{1}{\varepsilon_0} \cdot \frac{n}{lm} \cdot \left( \sum_{h=1}^{\lfloor n/d \rfloor} C_{Layer,h} \right)^{-1} \quad \text{Formula 2}$$

3 Claims, 13 Drawing Sheets

(56) References Cited

U.S. PATENT DOCUMENTS

| | | | |
|---|---|---|---|
| 10,422,763 B2 * | 9/2019 | Hidaka | G01R 27/2617 |
| 2004/0246079 A1 | 12/2004 | Ehata | |
| 2005/0093555 A1 | 5/2005 | Ehata | |
| 2009/0261847 A1 | 10/2009 | Petrovsky et al. | |
| 2010/0176824 A1 | 7/2010 | Makihara et al. | |

FOREIGN PATENT DOCUMENTS

| | | |
|---|---|---|
| CN | 104237648 A | 12/2014 |
| CN | 104407233 A | 3/2015 |
| JP | 52-85864 A | 7/1977 |
| JP | 2006-184209 A | 7/2006 |
| JP | 2008-157840 A | 7/2008 |
| JP | 2014-13228 A | 1/2014 |

OTHER PUBLICATIONS

Hidaka, "Powder Simulation Supporting the Progress of Powder Technology", Funtai Gijutsu, Dec. 1, 2010, vol. 2, No. 12, pp. 15-21, cited in ISR of PCT/JP2016/080229 (7 pages total).

Kushimoto et al., "Yudenritsu ni yoru Biryushi Composite Zairyochu no Biryushi Bunsan Jotai no Keisoku", Society of Powder Technology, Japan Kenkyu Happyokai Koen Ronbunshu, Oct. 8, 2013, vol. 2013 Shuki, pp. 100-101, cited in ISRs of PCT/JP2016/080229 and PCT/JP2016/080322 (6 pages total).

Moriyama et al., "Relationship between Indices of Dispersibility of Filler Particles Obtained by Image Analysis and Characteristics of Composite Materials Contained Filler Particles", Preprint of the Symposium on Powder Science and Technology, Sep. 28, 2015, vol. 53, pp. 139-143, cited in ISR of PCT/JP2016/080229 (7 pages total).

International Search Report dated Jan. 10, 2017, issued in counterpart International Application No. PCT/JP2016/080229 (2 pages).

International Search Report dated Jan. 10, 2017, issued in International Application No. PCT/JP2016/080322 (2 pages).

Extended (supplementary) European Search Report dated Apr. 9, 2019, issued in counterpart EP Application No. 16855451.7. (7 pages).

Notification of Transmittal of Translation of the International Preliminary Report on Patentability (Form PCT/IB/338) issued in counterpart International Application No. PCT/JP2016/080229 dated Apr. 26, 2018, with Forms PCT/IB/373 and PCT/ISA/237. (6 pages).

Extended (supplementary) European Search Report dated Jun. 12, 2019, issued in counterpart EP Application No. 16855419.4 (7 pages).

Notification of Transmittal of Translation of the International Preliminary Report on Patentability (Form PCT/IB/338) issued in International Application No. PCT/JP2016/080322 dated Apr. 26, 2018, with Forms PCT/IB/373 and PCT/ISA/237. (7 pages).

* cited by examiner ns in the z-axis direction are combined and layered in the z-axis direction and assigning a capacitance $C_{Layer,h}$ of each of the layers represented by Formula 1 below to Formula 2 below to determine a relative dielectric constant $\varepsilon_{Total}$ of the cell combination.

METHOD FOR CALCULATING DIELECTRIC CONSTANT OF PARTICLE-DISPERSED COMPOSITE MATERIALS AND METHOD FOR EVALUATING DISPERSIBILITY

TECHNICAL FIELD

The present invention relates to methods for calculating the dielectric constant of particle-dispersed composite materials and methods for evaluating dispersibility using the same.

BACKGROUND ART

As a method for evaluating the dispersibility in particle-dispersed composite materials containing particles dispersed in a medium, there is known, for example, a method for evaluating the dispersibility by image analysis using a microscope, such as an optical microscope, a scanning electron microscope, a transmission electron microscope or a laser microscope (see, for example, Patent Literature 1).

CITATION LIST

Patent Literature

Patent Literature 1: JP-A-2014-13228

SUMMARY OF INVENTION

Technical Problem

However, such a method has the problem that special samples for measurement are required, the problem that an evaluation device becomes complex and is thus increased in size, and so on.

An object of the present invention is to provide a method for calculating the dielectric constant of particle-dispersed composite materials that enables an easy evaluation of dispersibility and a method for evaluating the dispersibility using the same.

Solution to Problem

A method for calculating the dielectric constant according to the present invention is a method for calculating a dielectric constant of a particle-dispersed composite material containing particles dispersed in a medium and includes: measuring a number-based median particle diameter $D_{50}$, a maximum diameter $D_{max}$, a minimum diameter $D_{min}$ and a geometric standard deviation $\sigma_g$ in a particle diameter distribution of the particles in an unagglomerated state; assuming the particle-dispersed composite material as a cell combination in which unit cells having the same length a in each of an x-axis direction, a y-axis direction, and a z-axis direction are combined together in the x-axis direction, the y-axis direction, and the z-axis direction and which has a length l in the x-axis direction, a length m in the y-axis direction, and a length n in the z-axis direction, considering that each of the unit cells of the cell combination is constituted by a single particle element or a single medium element, and creating the cell combination in which the particle element or the medium element is assigned to each of the unit cells in consideration of the number-based median particle diameter $D_{50}$, the maximum diameter $D_{max}$, the minimum diameter $D_{min}$ and the geometric standard deviation $\sigma_g$ in the particle diameter distribution and a content of the particles in the particle-dispersed composite material; and calculating a relative dielectric constant of the particle-dispersed composite material by assuming the cell combination as a laminate in which layers having a thickness d in the z-axis direction are combined and layered in the z-axis direction and assigning a capacitance $C_{Layer,h}$ of each of the layers represented by Formula 1 below to Formula 2 below to determine a relative dielectric constant $\varepsilon_{Total}$ of the cell combination.

[Math. 1]

$$C_{Layer,h} = \left\{ \sum_{j=1}^{\lfloor m/a \rfloor} \sum_{i=1}^{\lfloor l/a \rfloor} \left( \sum_{k=1}^{\lfloor d/a \rfloor} \frac{1}{\varepsilon_{ijk} \varepsilon_0 a} \right)^{-1} \right\}^{-1} \quad \text{Formula 1}$$

$\varepsilon_0$: dielectric constant of vacuum (F/m)

[Math. 2]

$$\varepsilon_{Total} = \frac{1}{\varepsilon_0} \cdot \frac{n}{lm} \cdot \left( \sum_{h=1}^{\lfloor n/d \rfloor} C_{Layer,h} \right)^{-1} \quad \text{Formula 2}$$

In the present invention, the length a of the unit cell is preferably $a=(D_{50}/\beta\sigma_g)$ and a fitting parameter $\beta$ is selected within a range of values where determination results of the relative dielectric constant $\varepsilon_{Total}$ have a constant standard deviation.

A method for evaluating dispersibility according to the present invention is a method for evaluating dispersibility in a particle-dispersed composite material containing particles dispersed in a medium and includes the steps of: measuring a number-based median particle diameter $D_{50}$, a maximum diameter $D_{max}$, a minimum diameter $D_{min}$, and a geometric standard deviation $\sigma_g$ in a particle diameter distribution of the particles in an unagglomerated state; measuring a relative dielectric constant of the particle-dispersed composite material to obtain a measured value of the relative dielectric constant of the particle-dispersed composite material; and assuming arbitrary values as a volume content Va % of agglomerates in the particles and an average number Na of primary particles forming the agglomerates, determining the relative dielectric constant $\varepsilon_{Total}$ of the cell combination by the above-described method for calculating a dielectric constant according to the present invention, and selecting values of Va and Na giving a relative dielectric constant $\varepsilon_{Total}$ nearest to the measured value of the relative dielectric constant of the particle-dispersed composite material, wherein the dispersibility is evaluated by determining from the selected values of Va and Na a particle diameter distribution of the particles inclusive of the agglomerates in the particle-dispersed composite material.

Advantageous Effects of Invention

The present invention enables an easy calculation of the dielectric constant of a particle-dispersed composite material and an easy evaluation of dispersibility in the particle-dispersed composite material.

DESCRIPTION OF EMBODIMENTS

Hereinafter, a description will be given of a preferred embodiment. However, the following embodiment is merely illustrative and the present invention is not limited by the following embodiment.

Figure 1:
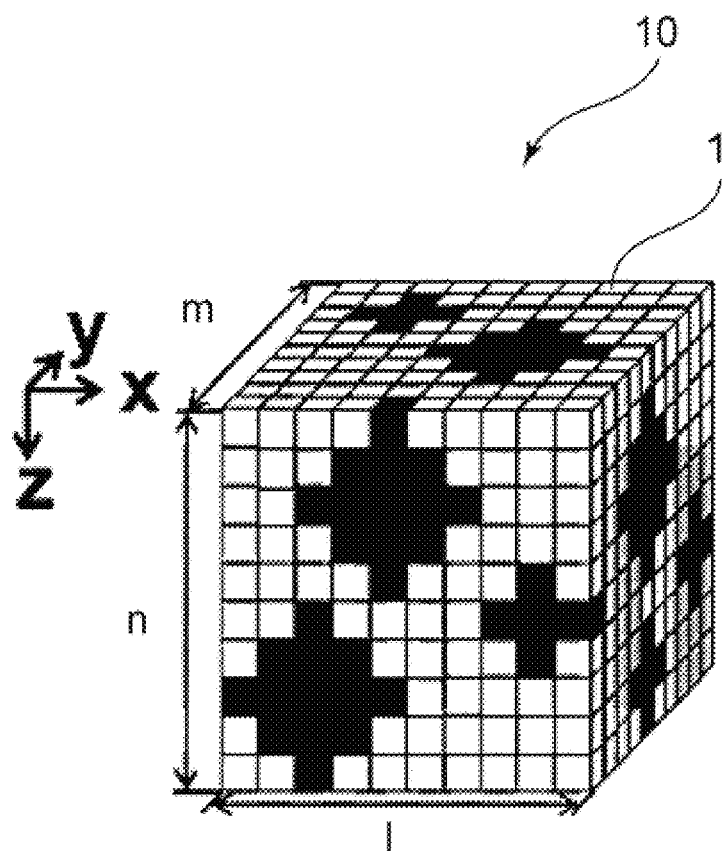
FIG. 1 is a perspective view for illustrating a cell combination assumed in the present invention.

FIG. 1 is a perspective view for illustrating a cell combination assumed in the present invention. In a method for calculating the dielectric constant according to the present invention, a particle-dispersed composite material is assumed as a cell combination 10 shown in FIG. 1. In the present invention, the particle-dispersed composite material is a composite material in which particles of an inorganic filler, an organic filler or others are dispersed in a medium, such as a resin or a polymer.

Figure 3:
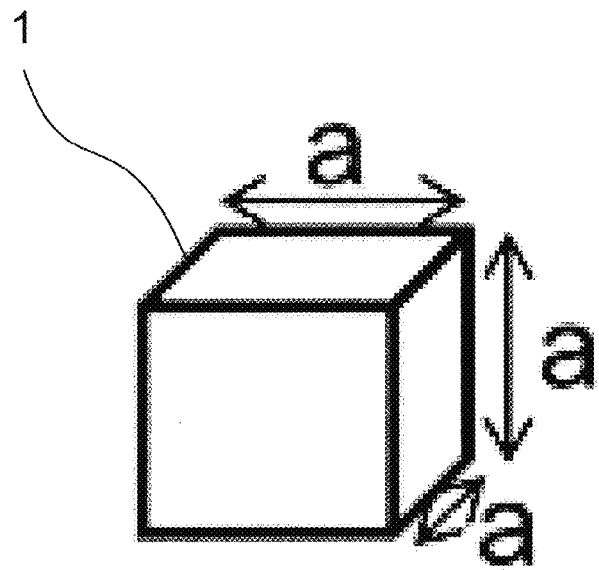
FIG. 3 is a perspective view showing a unit cell constituting part of the cell combination in the present invention.

The cell combination 10 shown in FIG. 1 is formed by combining unit cells 1 shown in FIG. 3 together in the x-axis direction, the y-axis direction, and the z-axis direction. As shown in FIG. 3, the unit cell 1 has the same length a in each of the x-axis direction, the y-axis direction, and the z-axis direction. In the cell combination 10 shown in FIG. 1, the unit cells 1 are combined together to form a length 1 in the x-axis direction, a length m in the y-axis direction, and a length n in the z-axis direction.

Figure 4:
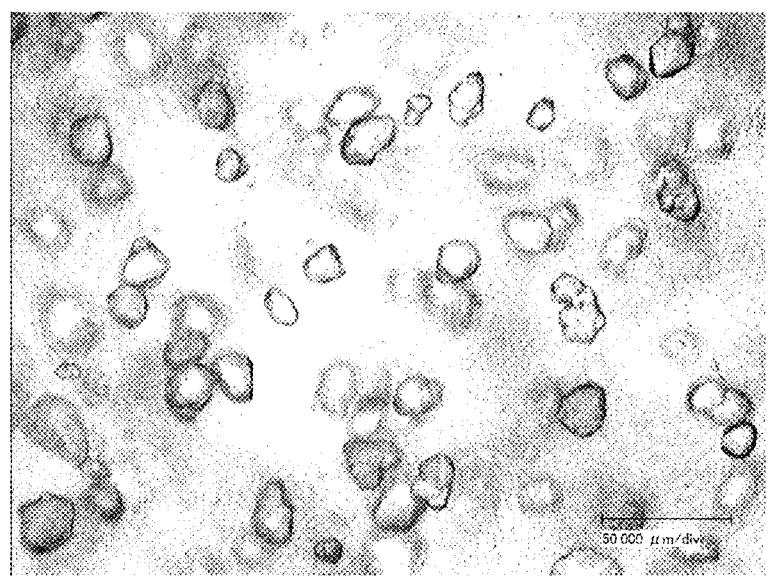
FIG. 4 is an optical micrograph of a particle-dispersed composite material having a content of particles of 5% by volume.
Figure 5:
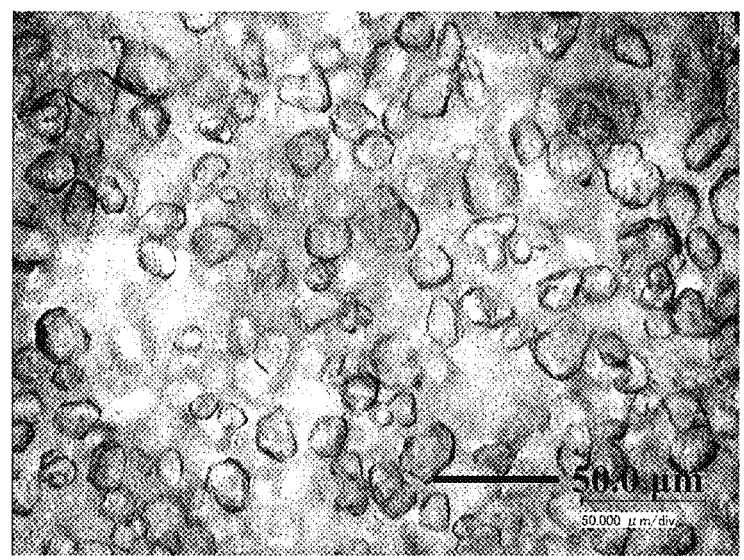
FIG. 5 is an optical micrograph of a particle-dispersed composite material having a content of particles of 20% by volume.

FIG. 4 is an optical micrograph of an example of a particle-dispersed composite material having a content of particles of 5% by volume. FIG. 5 is an optical micrograph of an example of a particle-dispersed composite material having a content of particles of 20% by volume. In these cases, alumina particles are used as particles and polyvinyl chloride (PVC) is used as a medium. As shown in FIGS. 4 and 5, there are observed particles in contact with each other and particles out of contact with each other. In the present invention, each set of particles in contact with each other are evaluated as an agglomerate. On the other hand, particles out of contact with each other are evaluated as disperse particles.

Figure 6:
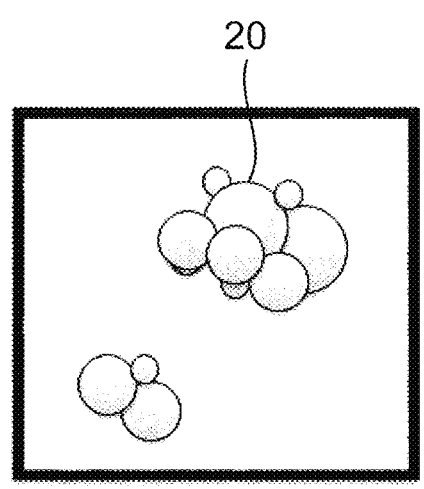
FIG. 6 is a perspective view showing particle agglomerates.
Figure 7:
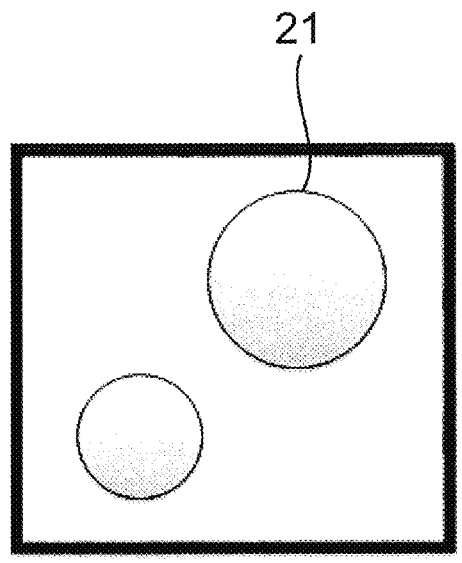
FIG. 7 is a perspective view showing particle agglomerate models in the present invention.

In the method for calculating the dielectric constant according to the present invention, each agglomerate 20 shown in FIG. 6 is treated as an agglomerate model 21 as shown in FIG. 7. Specifically, the agglomerate 20 is treated as a single particle (agglomerate model 21) having a larger diameter than single particles forming the agglomerate 20.

As shown in FIG. 1, in the cell combination 10, each unit cell 1 is considered to consist of a single element and a particle element or a medium element is assigned to each unit cell 1. In FIG. 1, black unit cells 1 represent unit cells 1 to which particle elements are assigned, while white unit cells 1 represent unit cells 1 to which medium elements are assigned.

In the present invention, the number-based median particle diameter $D_{50}$, the maximum diameter $D_{rmax}$, the minimum diameter $D_{min}$ and the geometric standard deviation $\sigma_g$ in a particle diameter distribution of particles in an unagglomerated state are previously measured. The particle diameter distribution of particles in an unagglomerated state can be determined, for example, by measuring the particle diameter distribution of particles in powder form. The particle diameter distribution in powder form can be measured, for example, by a laser diffraction particle size distribution analyzer or observation with a microscope or the like. In determining the particle diameter by observation with a microscope or the like, the Green diameter in a predetermined direction can be defined as the particle diameter.

In assigning a particle element or a medium element to each unit cell 1 of the cell combination 10, the particle element or the medium element is assigned to each unit cell 1 in consideration of the above number-based median particle diameter $D_{50}$, maximum diameter $D_{max}$, minimum diameter $D_{min}$, and geometric standard deviation $\sigma_g$ in the particle diameter distribution and the content of particles in the particle-dispersed composite material.

As for the cell combination 10 in which particle elements or medium elements are assigned to the unit cells 1 in the above manner, its dielectric constant is calculated. In calculating the dielectric constant of the cell combination 10 in the present invention, the cell combination 10 is assumed as a laminate in which layers having a thickness d in the z-axis direction are combined and layered in the z-axis direction.

Figure 2:
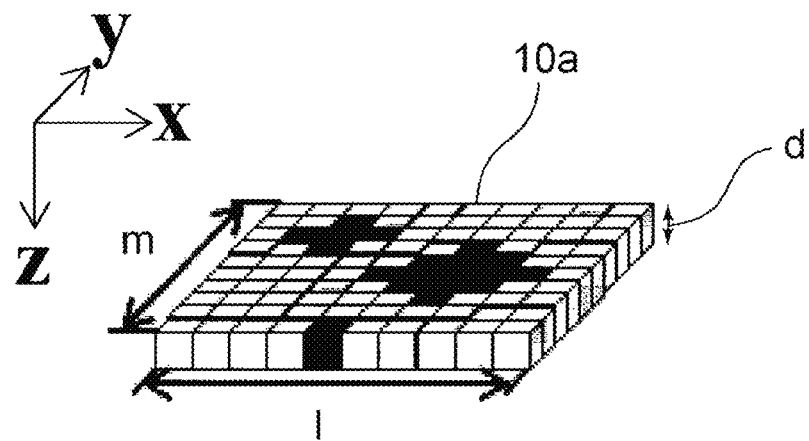
FIG. 2 is a perspective view for illustrating a layer assumed in determining the dielectric constant of the cell combination in the present invention.

FIG. 2 is a perspective view showing a layer constituting part of the above laminate. As shown in FIG. 2, the layer 10a has a thickness d in the z-direction. Furthermore, its length in the x-direction is l and its length in the y-direction is m. When the layers 10a shown in FIG. 2 are combined in the z-axis direction, the cell combination 10 shown in FIG. 1 is formed.

No particular limitation is placed on the thickness d of the layer 10a, but d represented by the following formula is preferably used.

$$d = (D_4 \sigma_g)/2(1+P_f)$$

$D_4$: volume mean diameter (μm)
$P_f$: volume content of particles (within a range of 0 to 1)
The volume mean diameter $D_4$ and the geometric standard deviation $\sigma_g$ are defined by the following formulas.

$$D_4 = D_{4,D}(1-V_{aN}/100) + D_{4,A}V_{aN}/100$$

$$\sigma_g = \sigma_{g,D}(1-V_{aN}/100) + \sigma_{g,A}V_{aN}/100$$

Suffix D: group of unagglomerated (dispersed) particles
Suffix A: group of agglomerated particles
$V_{aN}$: percentage of number of agglomerates
The capacitance $C_{Layer,h}$ of the layer 10a (the capacitance of the h-th layer) can be represented by the following Formula 1.

[Math. 1]

$$C_{Layer,h} = \left\{ \sum_{j=1}^{\lfloor m/a \rfloor} \sum_{i=1}^{\lfloor l/a \rfloor} \left( \sum_{k=1}^{\lfloor d/a \rfloor} \frac{1}{\varepsilon_{ijk}\varepsilon_0 a} \right)^{-1} \right\}^{-1} \quad \text{Formula 1}$$

Figure 8:
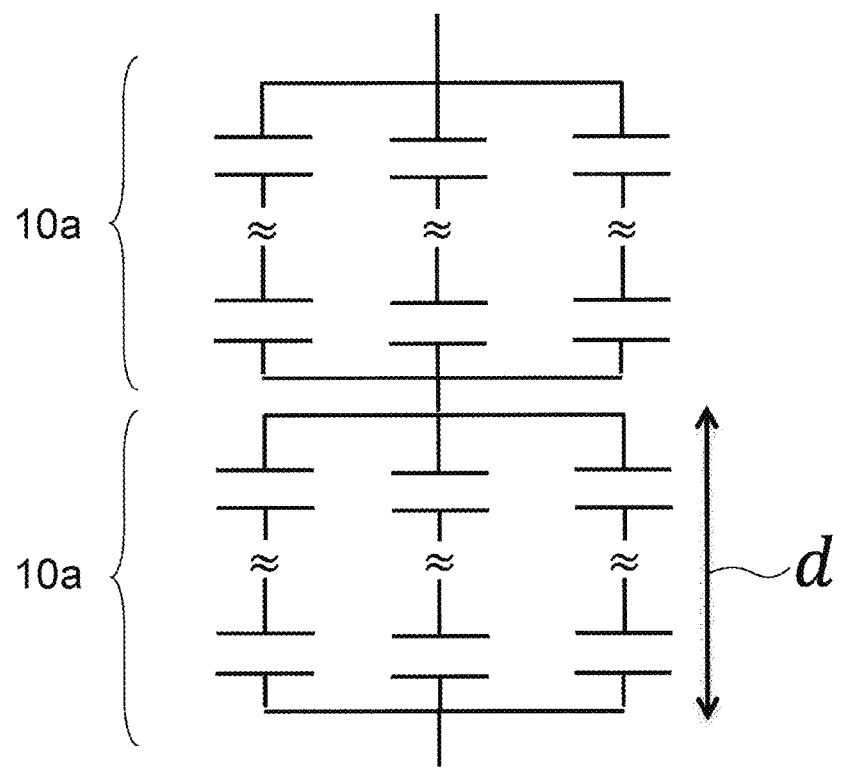
FIG. 8 is a diagram showing an electric circuit model of a laminate of layers constituting the cell combination.

$\varepsilon_0$: dielectric constant of vacuum (F/m)
Note that the unit of the lengths l, m, and n is μm.
FIG. 8 is a diagram showing an electric circuit model of a laminate of layers 10a constituting the cell combination 10. The relative dielectric constant $\varepsilon_{Total}$ of the cell combination 10 can be determined by assigning the capacitance $C_{Layer,h}$ of each layer 10a to the following Formula 2.

[Math. 2]

$$\varepsilon_{Total} = \frac{1}{\varepsilon_0} \cdot \frac{n}{lm} \cdot \left( \sum_{h=1}^{\lfloor n/d \rfloor} C_{Layer,h} \right)^{-1} \quad \text{Formula 2}$$

According to the present invention, the relative dielectric constant of the particle-dispersed composite material can be calculated by determining the relative dielectric constant $\varepsilon_{Total}$ of the cell combination 10 in the above manner.

Although an arbitrary value can be used as the length a of the unit cell 1, a value of a determined by the following formula is preferably used.

$$a = (D_{50}/\beta\sigma_g)$$

$\beta$: fitting parameter
An optimal fitting parameter $\beta$ was determined under the conditions shown in Table 1. The fitting parameter $\beta$ was changed within a range of 2 to 30.

TABLE 1

| | | |
|---|---|---|
| System Size | l (x-direction) | 30 (μm) |
| | m (y-direction) | 30 (μm) |
| | n (z-direction) | 30 (μm) |
| Unit Cell Length | a | $D_{50}/\beta\sigma g$ ($\beta$ = 2~30) |
| Particle Diameter | Max. Diameter Dmax | 1.69 (μm) |
| Distribution | Min. Diameter Dmin | 0.35 (μm) |
| | Median Diameter $D_{50}$ | 0.77 (μm) |
| | Geom. Standard Deviation | 1.47 (—) |
| Dielectric Constant of Vacuum | | 8.854 × 10⁻¹² (Fm⁻¹) |
| Dielectric Constant of Medium | | 2.227 (—) |
| Dielectric Constant of Particles | | 100 (—) |
| Volume Content of Particles | | 10 (%) |

Figure 9:
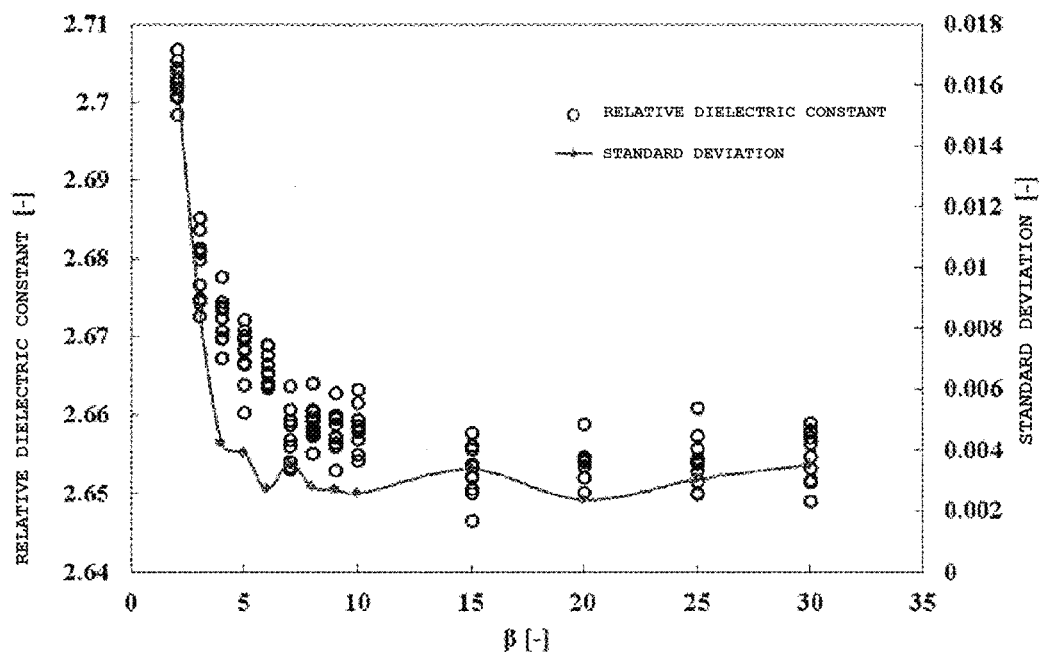
FIG. 9 is a graph showing results of simulation for determining the length of the unit cell.

FIG. 9 is a graph showing results of simulation for determining the length a of the unit cell. As shown in FIG. 9, the standard deviation of the relative dielectric constant is constant when the fitting parameter $\beta$ is within a range of 10 to 30. To reduce the computational load, the value 10 was adopted as the fitting parameter $\beta$ in the simulations below.

Next, an optimal number of unit cells was determined under the conditions shown in Table 2. The number of unit cells was changed within a range of 100 to 2000. Furthermore, the volume content of particles was changed within a range of 0 to 15% by volume.

TABLE 2

| | | |
|---|---|---|
| Number of Cells | l/a (x-direction) | 100~2000 (—) |
| | m/a (y-direction) | 100~2000 (—) |
| | n/a (z-direction) | 100~2000 (—) |
| Unit Cell Length | a | $D_{50}/10\sigma g$ |
| Particle Diameter | Max. Diameter Dmax | 1.69 (μm) |
| Distribution | Min. Diameter Dmin | 0.35 (μm) |
| | Median Diameter $D_{50}$ | 0.77 (μm) |
| | Geom. Standard Deviation | 1.47 (—) |
| Dielectric Constant of Vacuum | | 8.854 × 10⁻¹² (Fm⁻¹) |
| Dielectric Constant of Medium | | 134 (—) |
| Dielectric Constant of Particles | | 7.4 (—) |
| Volume Content of Particles | | 0~15 (%) |

Figure 10:
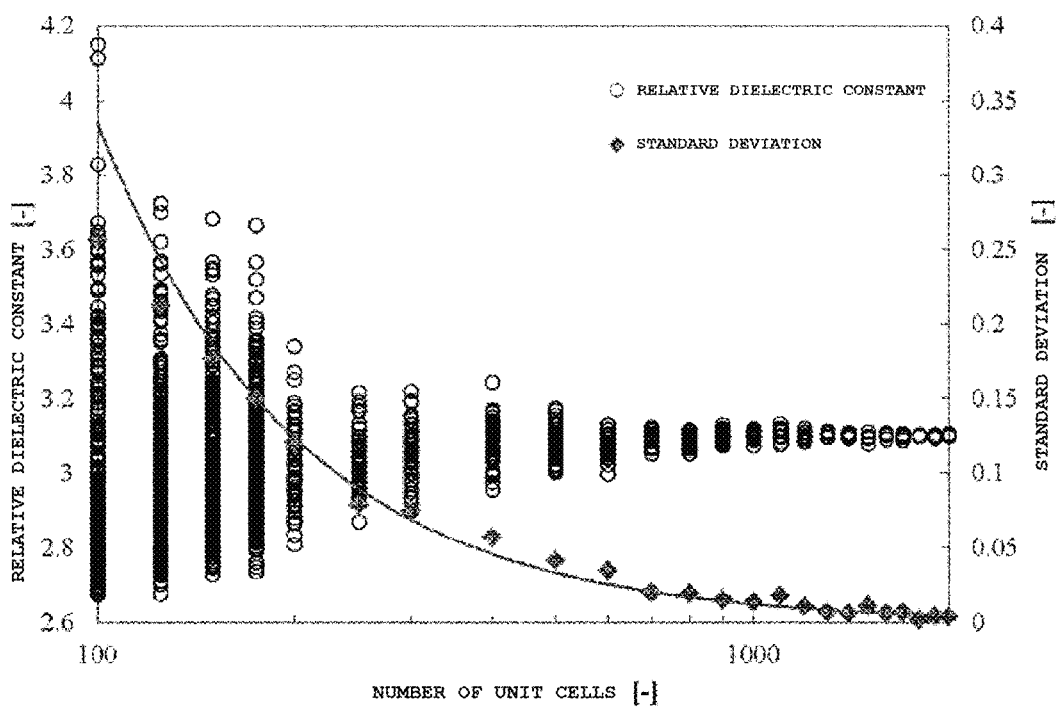
FIG. 10 is a graph showing results of simulation for determining the number of unit cells.

FIG. 10 is a graph showing results of simulation for determining the number of unit cells. As shown in FIG. 10, when the number of unit cells is 1000 or more, the standard deviation of the relative dielectric constant is around 0.01. In the simulations below, the number of unit cells was set at 1500 on the safe side.

(Calculation of Dielectric Constant of Particle-Dispersed Composite Material)
<Sample 1>
In Sample 1, glass beads were used as particles and gelatin was used as a medium. The relative dielectric constant of the glass beads was set at 7.4 and the dielectric constant of gelatin was set at 134. The number-based median particle diameter $D_{50}$, the maximum diameter $D_{max}$, the minimum diameter $D_{min}$ and the geometric standard deviation $\sigma_g$ in a particle diameter distribution of unagglomerated glass beads are as shown in Table 3.

TABLE 3

| Number of Cells | l/a (x-direction) | 1500 | (—) |
|---|---|---|---|
| | m/a (y-direction) | 1500 | (—) |
| | n/a (z-direction) | 1500 | (—) |
| Unit Cell length | a | $D_{50}/10\sigma g$ | |
| Particle Diameter Distribution | Max. Diameter Dmax | 1090 | (μm) |
| | Min. Diameter Dmin | 480 | (μm) |
| | Median Diameter $D_{50}$ | 720 | (μm) |
| | Geom. Standard Deviation | 1.22 | (—) |
| | Dielectric Constant of Vacuum | $8.854 \times 10^{-12}$ | (Fm$^{-1}$) |
| | Dielectric Constant of Medium | 134 | (—) |
| | Dielectric Constant of Particles | 7.4 | (—) |
| | Volume Content of Particles | 0~15 | (%) |

Figure 11:
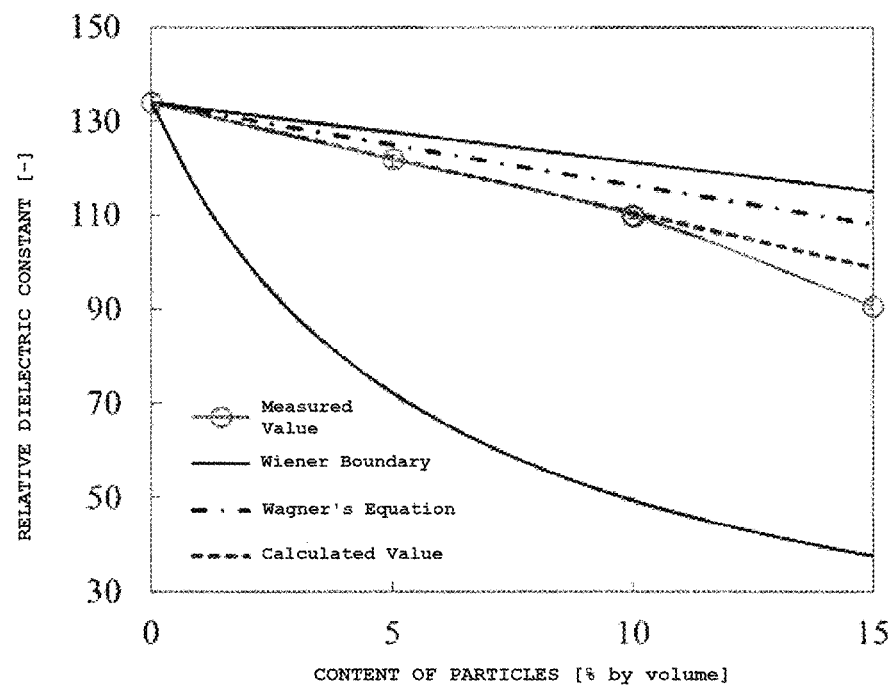
FIG. 11 is a graph showing the relation between content of particles and relative dielectric constant in Sample 1.

FIG. 11 is a graph showing measured values, calculated values, and the Wiener boundary of the relative dielectric constant of Sample 1 and its relative dielectric constant values based on the Wagner's equation and shows the relation between content of particles and relative dielectric constant. The measured values of the relative dielectric constant were measured using an LCR meter. The calculated values of the relative dielectric constant were calculated based on the above simulation. The direction of an electric field applied was the z-direction. The values based on the Wagner's equation are described in detail, for example, in Tetsuya Hanai "Fukinshitsukouzo to Yudenritsu/Busshitsu wo kowasazu ni Naibukouzo wo saguru", Yoshioka Shoten.

As shown in FIG. 11, the calculated values of the relative dielectric constant calculated according to the present invention are approximate to the actually measured values thereof. Furthermore, it can be seen that the calculated values of the relative dielectric constant are within the Wiener boundary and, therefore, the simulation has validity. Moreover, it can be seen that the calculated values of the relative dielectric constant are also approximate to the values based on the Wagner's equation.

<Sample 2>

In Sample 2, zirconia (ZrO$_2$) particles were used as particles and an ultraviolet curable resin was used as a medium. The relative dielectric constant of zirconia was set at 27 and the dielectric constant of the ultraviolet curable resin was set at 3.57. The number-based median particle diameter $D_{50}$, the maximum diameter $D_{max}$, the minimum diameter $D_{min}$, and the geometric standard deviation $\sigma_g$ in a particle diameter distribution of unagglomerated zirconia particles are as shown in Table 4.

TABLE 4

| Number of Cells | l/a (x-direction) | 1500 | (—) |
|---|---|---|---|
| | m/a (y-direction) | 1500 | (—) |
| | n/a (z-direction) | 1500 | (—) |
| Unit Cell Length | a | $D_{50}/10\sigma g$ | |
| Particle Diameter Distribution | Max. Diameter Dmax | 2075 | (μm) |
| | Min. Diameter Dmin | 1814 | (μm) |
| | Median Diameter $D_{50}$ | 1940 | (μm) |
| | Geom. Standard Deviation | 1.03 | (μm) |
| | Dielectric Constant of Vacuum | $8.854 \times 10^{-12}$ | (Fm$^{-1}$) |
| | Dielectric Constant of Medium | 3.57 | (—) |
| | Dielectric Constant of Particles | 27 | (—) |
| | Volume Content of Particles | 0~5.2 | (%) |

Figure 12:
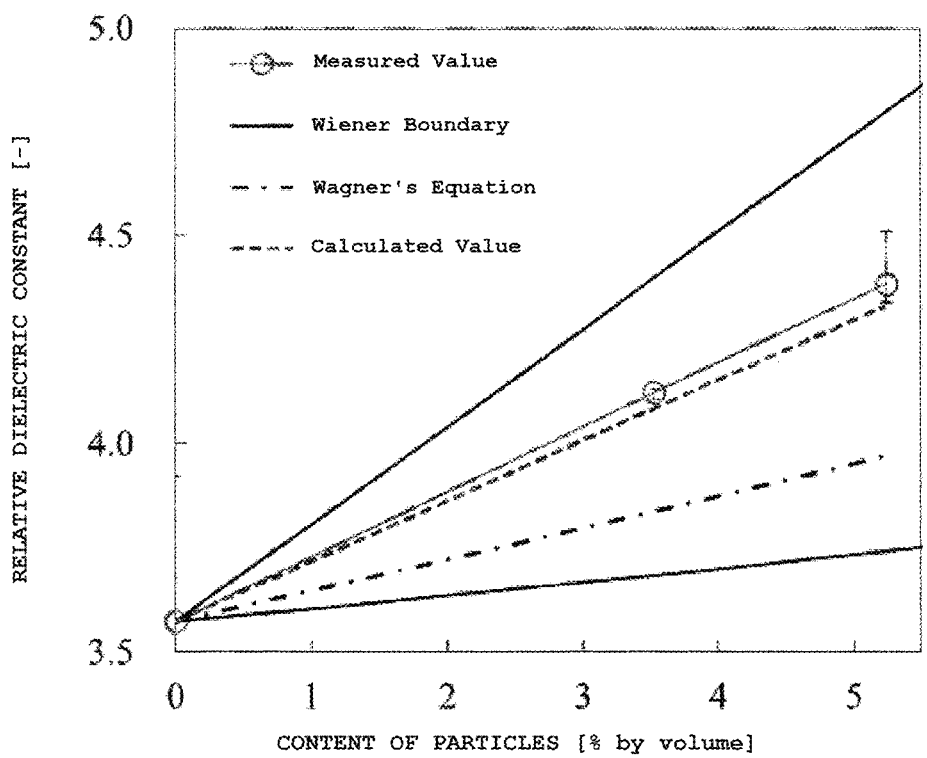
FIG. 12 is a graph showing the relation between content of particles and relative dielectric constant in Sample 2.

FIG. 12 is a graph showing measured values, calculated values, and the Wiener boundary of the relative dielectric constant of Sample 2 and its relative dielectric constant values based on the Wagner's equation and shows the relation between content of particles and relative dielectric constant.

As shown in FIG. 12, the calculated values of the relative dielectric constant calculated according to the present invention are approximate to the actually measured values thereof. Furthermore, it can be seen that the calculated values of the relative dielectric constant are within the Wiener boundary and, therefore, the simulation has validity. Moreover, it can be seen that the calculated values of the relative dielectric constant are also approximate to the values based on the Wagner's equation.

<Sample 3>

In Sample 3, alumina (Al$_2$O$_3$) particles were used as particles and polyvinyl chloride (PVC) was used as a medium. The relative dielectric constant of alumina was set at 9 and the dielectric constant of polyvinyl chloride was set at 4.07. The number-based median particle diameter $D_{50}$, the maximum diameter $D_{max}$, the minimum diameter $D_{min}$, and the geometric standard deviation $\sigma_g$ in a particle diameter distribution of unagglomerated alumina particles are as shown in Table 5.

TABLE 5

| Number of Cells | l/a (x-direction) | 1500 | (—) |
|---|---|---|---|
| | m/a (y-direction) | 1500 | (—) |
| | n/a (z-direction) | 1500 | (—) |
| Unit Cell Length | a | $D_{50}/10\sigma g$ | |
| Particle Diameter Distribution | Max. Diameter Dmax | 24.8 | (μm) |
| | Min. Diameter Dmin | 9.4 | (μm) |
| | Median Diameter $D_{50}$ | 15.2 | (μm) |
| | Geom. Standard Deviation | 1.27 | (μm) |
| | Dielectric Constant of Vacuum | $8.854 \times 10^{-12}$ | (Fm$^{-1}$) |
| | Dielectric Constant of Medium | 4.07 | (—) |
| | Dielectric Constant of Particles | 9 | (—) |
| | Volume Content of Particles | 0~20 | (%) |

Figure 13:
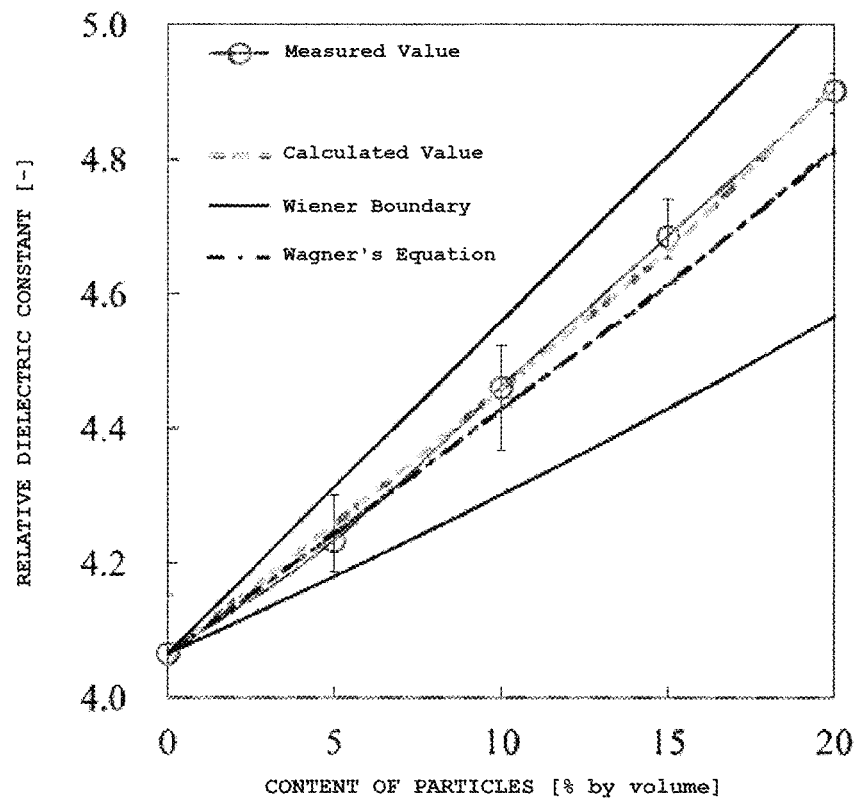
FIG. 13 is a graph showing the relation between content of particles and relative dielectric constant in Sample 3.
Figure 14:
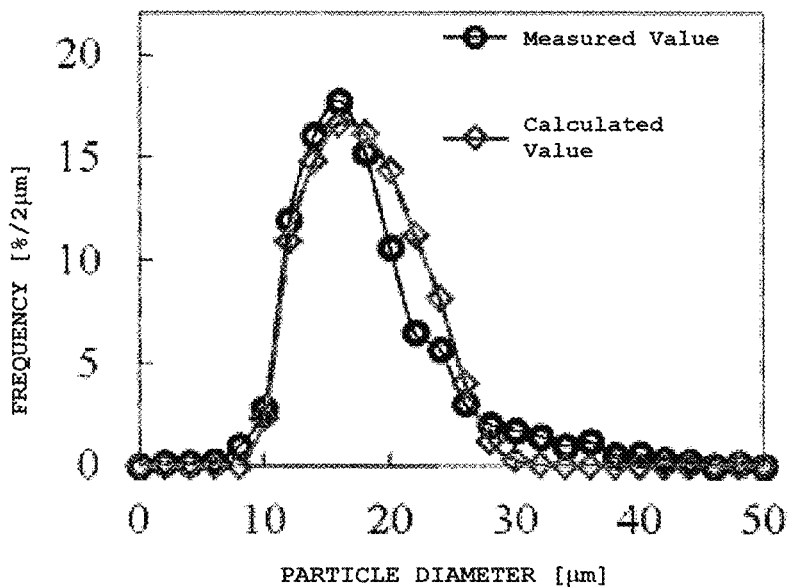
FIG. 14 is a graph showing a particle diameter distribution of measured values and a particle diameter distribution of calculated values in a particle-dispersed composite material having a content of particles of 5% by volume.
Figure 15:
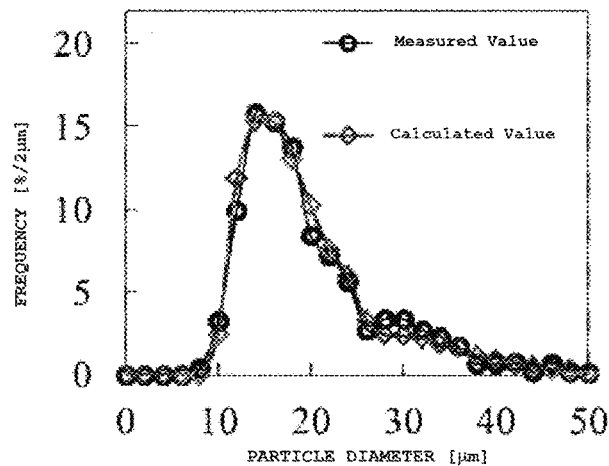
FIG. 15 is a graph showing a particle diameter distribution of measured values and a particle diameter distribution of calculated values in a particle-dispersed composite material having a content of particles of 10% by volume.
Figure 16:
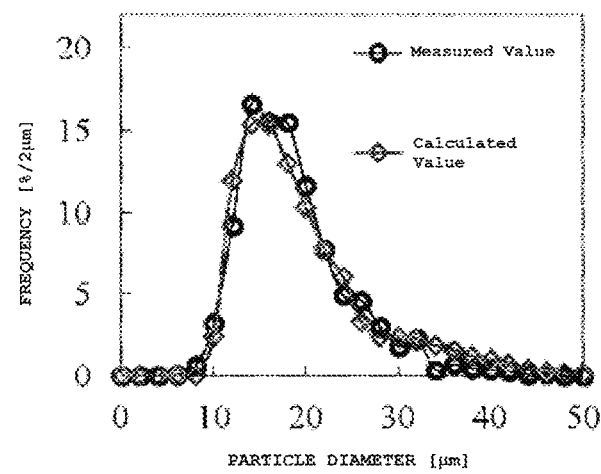
FIG. 16 is a graph showing a particle diameter distribution of measured values and a particle diameter distribution of calculated values in a particle-dispersed composite material having a content of particles of 15% by volume.
Figure 17:
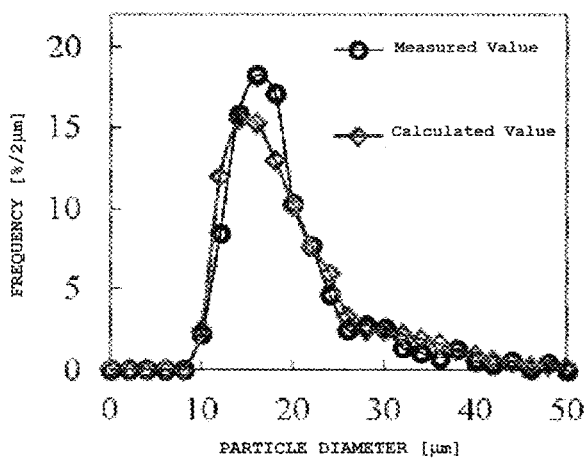
FIG. 17 is a graph showing a particle diameter distribution of measured values and a particle diameter distribution of calculated values in a particle-dispersed composite material having a content of particles of 20% by volume.

FIG. 13 is a graph showing measured values, calculated values, and the Wiener boundary of the relative dielectric constant of Sample 3 and its relative dielectric constant values based on the Wagner's equation and shows the relation between content of particles and relative dielectric constant.

As shown in FIG. 13, the calculated values of the relative dielectric constant calculated according to the present invention are approximate to the actually measured values thereof. Furthermore, it can be seen that the calculated values of the relative dielectric constant are within the Wiener boundary and, therefore, the simulation has validity. Moreover, it can be seen that the calculated values of the relative dielectric constant are also approximate to the values based on the Wagner's equation.

As thus far described, it can be seen that the method for calculating a dielectric constant according to the present invention enables an easy calculation of a value of the relative dielectric constant close to an actual measured value.

(Evaluation of Dispersibility in Particle-Dispersed Composite Material)

In a method for evaluating dispersibility according to the present invention, arbitrary values are assumed as a volume content Va % of agglomerates in the whole of particles and an average number Na of primary particles forming the agglomerates, the relative dielectric constant $\varepsilon_{Total}$ of a cell combination is determined by the above-described method for calculating a dielectric constant according to the present invention, and values of Va and Na giving a relative dielectric constant $\varepsilon_{Total}$ nearest to the measured value of the relative dielectric constant of a particle-dispersed composite material are selected. The dispersibility is evaluated by determining from the selected values of Va and Na a particle diameter distribution of the particles inclusive of the agglomerates in the particle-dispersed composite material.

The particle-dispersed composite material in Sample 3 above was used as a sample for evaluating dispersibility. Therefore, alumina ($Al_2O_3$) particles were used as particles and polyvinyl chloride (PVC) was used as a medium.

By changing the content of alumina particles to 5% by volume, 10% by volume, 15% by volume, and 20% by volume, four types of polyvinyl chloride resin compositions containing alumina particles dispersed therein were produced. These polyvinyl chloride resin compositions were measured in terms of relative dielectric constant with an LCR meter.

Arbitrary values were assumed as a volume content Va % of agglomerates in the whole of particles and an average number Na of primary particles forming the agglomerates and simulation was performed under the conditions shown in Table 5, thus determining the respective relative dielectric constants $\varepsilon_{Total}$ of four types of cell combinations having different contents of alumina particles. This simulation was repeatedly performed and the values of Va and Na giving nearest values to the respective measured values of the relative dielectric constants of the four types of polyvinyl chloride resin compositions were selected. The selected values of Va and Na are shown in Table 6.

TABLE 6

| $Al_2O_3$ Content (% by Volume) | Va (% by Volume) | Na (—) |
|---|---|---|
| 5 | 66.0 | 1.5 |
| 10 | 69.6 | 4.2 |
| 15 | 73.4 | 8.3 |
| 20 | 72.7 | 7.8 |

The particle diameter distributions in the particle-dispersed composite materials were each calculated from the values of Va and Na shown in Table 6, the number-based median particle diameter $D_{50}$, maximum diameter $D_{max}$, minimum diameter $D_{min}$, and geometric standard deviation $\sigma_g$ in the particle diameter distribution of particles in an unagglomerated state and the content of the particles in the particle-dispersed composite material. The resultant particle diameter distributions are shown as calculated values in FIGS. 14 to 17. Note that FIGS. 14, 15, 16, and 17 correspond to respective particle diameter distributions when the content of particles is 5% by volume, 10% by volume, 15% by volume, and 20% by volume, respectively.

Furthermore, the above four types of polyvinyl chloride resin compositions were measured in terms of particle diameter distribution in their actual composition using an optical microscope. The measured particle diameter distributions are shown as measured values in FIGS. 14 to 17.

As shown in FIGS. 14 to 17, the calculated values of each particle diameter distribution are very approximate to the measured values thereof, which shows that the method for evaluating dispersibility according to the present invention enables an easy and accurate evaluation of dispersibility of particles in a particle-dispersed composite material.

Figure 18:
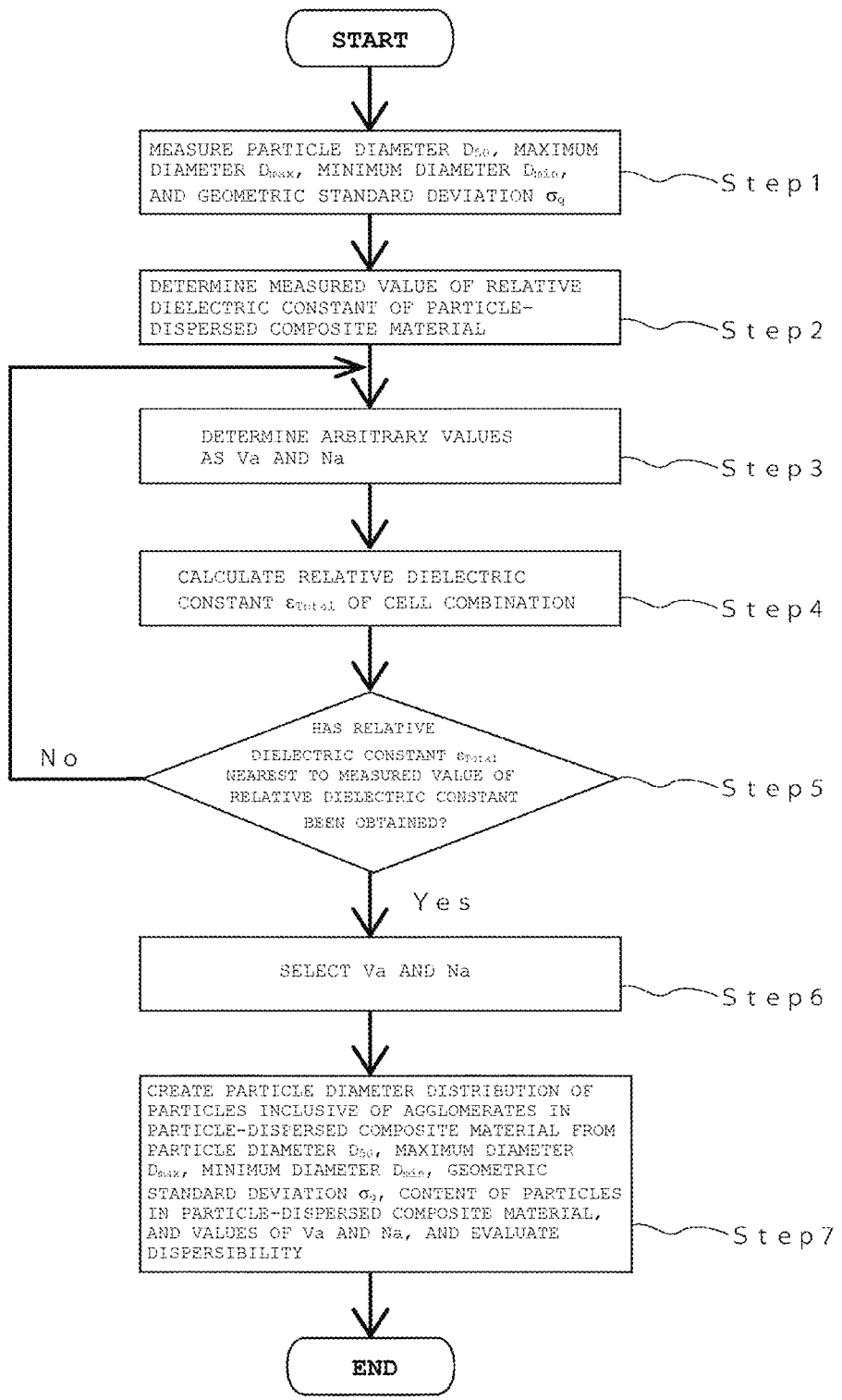
FIG. 18 is a flowchart showing an example of a method for evaluating dispersibility according to the present invention.

FIG. 18 is a flowchart showing an example of the method for evaluating dispersibility according to the present invention.

(Step 1)

The number-based median particle diameter $D_{50}$, the maximum diameter $D_{max}$, the minimum diameter $D_{min}$, and the geometric standard deviation $\sigma_g$ in a particle diameter distribution of particles in an unagglomerated state are measured.

(Step 2)

The relative dielectric constant of the particle-dispersed composite material is measured to obtain a measured value of the relative dielectric constant of the particle-dispersed composite material.

(Step 3)

Arbitrary values are determined as the volume content Va % of agglomerates in the particles and the average number Na of primary particles forming the agglomerates.

(Step 4)

Based on the above-described method for calculating a dielectric constant according to the present invention, the relative dielectric constant $\varepsilon_{Total}$ of the cell combination is calculated using the determined values of Va and Na, the number-based median particle diameter $D_{50}$, maximum diameter $D_{max}$, minimum diameter $D_{min}$, and geometric standard deviation $\sigma_g$ in the particle diameter distribution of the particles in an unagglomerated state and the content of the particles in the particle-dispersed composite material.

(Step 5)

A comparison is made between the calculated relative dielectric constant $\varepsilon_{Total}$ and the measured value of the relative dielectric constant and (Step 3) and (Step 4) are repeated until it is confirmed that a relative dielectric constant $\varepsilon_{Total}$ nearest to the measured value of the relative dielectric constant has been obtained.

(Step 6)

The values of Va and Na giving a relative dielectric constant $\varepsilon_{Total}$ nearest to the measured value of the relative dielectric constant are selected.

(Step 7)

A particle diameter distribution of the particles inclusive of the agglomerates in the particle-dispersed composite material is created from the particle diameter $D_{50}$, the maximum diameter $D_{max}$, the minimum diameter $D_{min}$, the geometric standard deviation $\sigma_g$, the content of the particles in the particle-dispersed composite material, and the selected values of Va and Na, and dispersibility in the particle-dispersed composite material is evaluated.

In the case where a plurality of values are calculated as each of Va and Na giving a value nearest to the measured value of the relative dielectric constant in the above method for evaluating dispersibility, values of Va and Na considered to be most suitable are selected in consideration of the number-based median particle diameter $D_{50}$, maximum diameter $D_{max}$, minimum diameter $D_{min}$, and geometric standard deviation $\sigma_g$ in the particle diameter distribution, the content of particles in the particle-dispersed composite material, and so on.

<Another Method for Determining Fitting Parameter β>

In the above method for determining the fitting parameter β, the fitting parameter β is determined within a range of values where the standard deviation of the relative dielectric constant is constant, i.e., within a range of values where variations in relative dielectric constant are sufficiently small. However, in the case of a system in which the difference in dielectric constant between particles and a medium is not so large, it may be difficult to examine the fitting parameter β based on variations in relative dielectric constant. As another method for determining the fitting parameter β, a method for determining the fitting parameter β within a range of values where variations in calculated volume content of particles are sufficiently small may be adopted.

Figure 19:
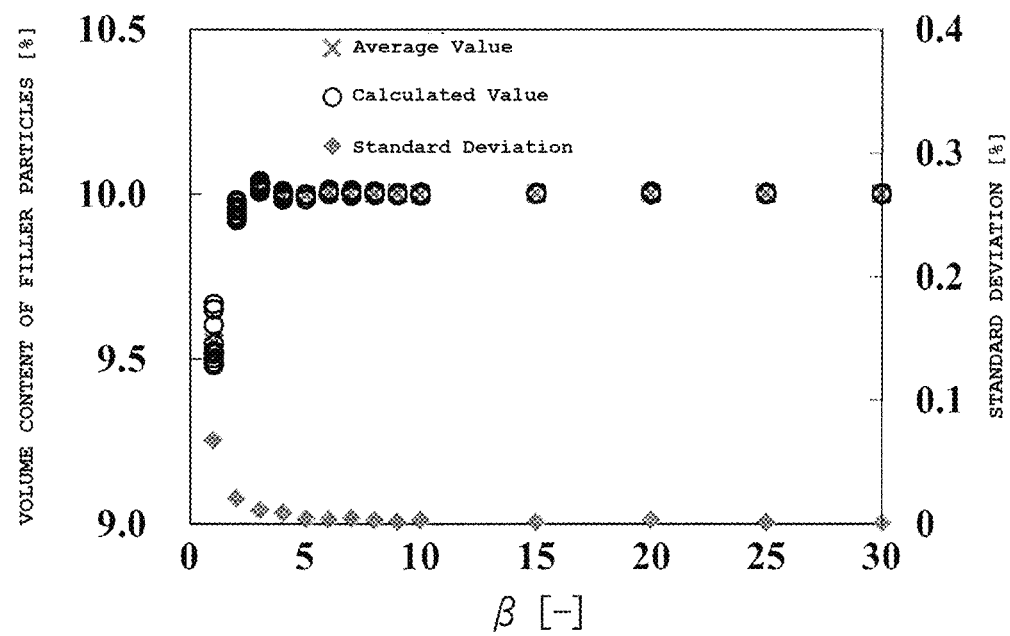
FIG. 19 is a graph showing simulation results of calculated volume contents of particles and their standard deviations.

FIG. 19 is a graph showing simulation results of calculated volume contents of particles and their standard deviations. As shown in FIG. 19, the standard deviation of the volume content is small when the fitting parameter β is within a range of 10 to 30. Therefore, like the method described previously, the value 10 can be adopted as the fitting parameter β.

(Calculation of Dielectric Constant of Particle-Dispersed Composite Material)

<Sample 4>

In Sample 4, alumina beads were used as particles and gelatin was used as a medium. The relative dielectric constant of the alumina beads was set at 9 and the dielectric constant of gelatin was set at 112. The number-based median particle diameter $D_{50}$, the maximum diameter $D_{max}$, the minimum diameter $D_{min}$, and the geometric standard deviation $\sigma_g$ in a particle diameter distribution of unagglomerated alumina beads are as shown in Table 7.

TABLE 7

| Number of Cells | l/a (x-direction) | 3178 | (—) |
|---|---|---|---|
| | m/a (y-direction) | 3178 | (—) |
| | n/a (z-direction) | 172~188 | (—) |
| Unit Cell Length | a | $D_{50}/10\sigma g$ | |
| Particle Diameter Distribution | Max. Diameter Dmax | 2140 | (μm) |
| | Min. Diameter Dmin | 970 | (μm) |
| | Median Diameter $D_{50}$ | 1440 | (μm) |
| | Geom. Standard Deviation | 1.22 | (—) |
| Dielectric Constant of Vacuum | | $8.854 \times 10^{-12}$ | (Fm$^{-1}$) |
| Dielectric Constant of Medium | | 112 | (—) |
| Dielectric Constant of Particles | | 9 | (—) |
| Volume Content of Particles | | 0~11.1 | (%) |

Figure 20:
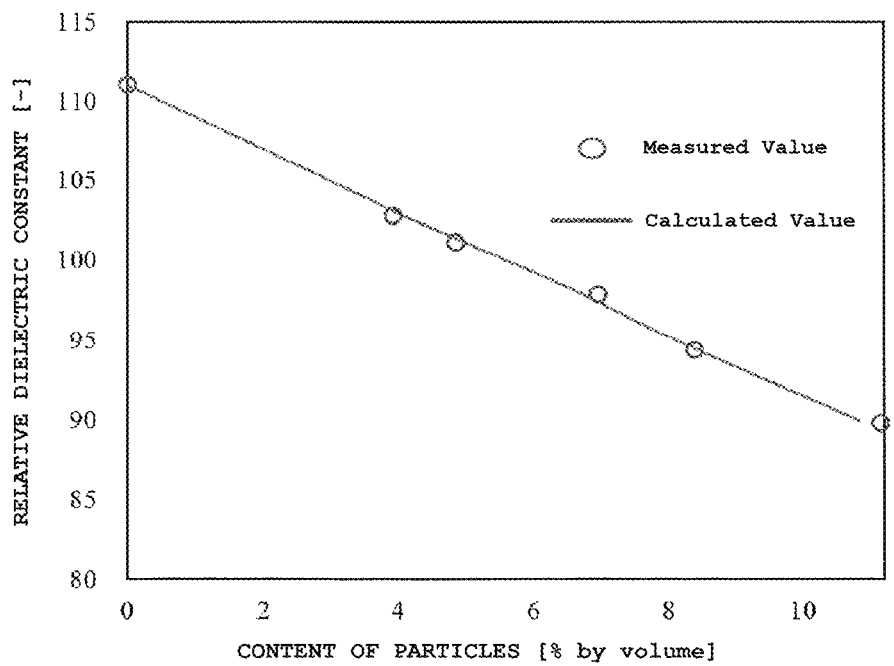
FIG. 20 is a graph showing the relation between content of particles and relative dielectric constant in Sample 4.

FIG. 20 is a graph showing measured values and calculated values of the relative dielectric constant of Sample 4 and shows the relation between content of particles and relative dielectric constant. The measured values of the relative dielectric constant were measured using an LCR meter. The calculated values of the relative dielectric constant were calculated from the above simulation. The direction of an electric field applied was the z-direction.

As shown in FIG. 20, the calculated values of the relative dielectric constant calculated according to the present invention are approximate to the actually measured values thereof.

<Sample 5>

In Sample 5, alumina balls were used as particles and epoxy resin was used as a medium. The relative dielectric constant of alumina balls was set at 9 and the dielectric constant of epoxy resin was set at 4.44. The number-based median particle diameter $D_{50}$, the maximum diameter $D_{max}$, the minimum diameter $D_{min}$, and the geometric standard deviation $\sigma_g$ in a particle diameter distribution of unagglomerated alumina balls are as shown in Table 8.

TABLE 8

| Number of Cells | l/a (x-direction) | 2645 | (—) |
|---|---|---|---|
| | m/a (y-direction) | 2645 | (—) |
| | n/a (z-direction) | 552~695 | (—) |
| Unit Cell Length | a | $D_{50}/10\sigma g$ | |
| Particle Diameter Distribution | Max. Diameter Dmax | 5300 | (μm) |
| | Min. Diameter Dmin | 4890 | (μm) |
| | Median Diameter $D_{50}$ | 5090 | (μm) |
| | Geom. Standard Deviation | 1.02 | (μm) |
| Dielectric Constant of Vacuum | | $8.854 \times 10^{-12}$ | (Fm$^{-1}$) |
| Dielectrtic Constant of Medium | | 4.44 | (—) |
| Dielectric Constant of Particles | | 9 | (—) |
| Volume Content of Particles | | 0~15.2 | (%) |

Figure 21:
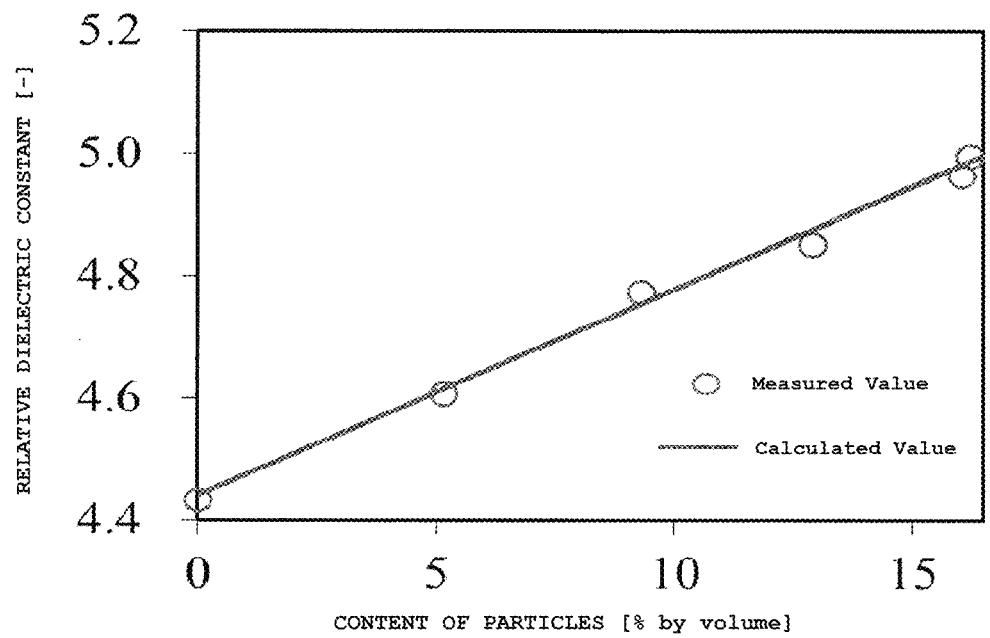
FIG. 21 is a graph showing the relation between content of particles and relative dielectric constant in Sample 5.

FIG. 21 is a graph showing measured values and calculated values of the relative dielectric constant of Sample 5 and shows the relation between content of particles and relative dielectric constant.

As shown in FIG. 21, the calculated values of the relative dielectric constant calculated according to the present invention are approximate to the actually measured values thereof.

<Sample 6>

In Sample 6, alumina ($Al_2O_3$) particles were used as particles and polyvinyl chloride (PVC) was used as a medium. The relative dielectric constant of alumina was set at 9 and the dielectric constant of polyvinyl chloride was set at 3.78. The number-based median particle diameter $D_{50}$, the maximum diameter $D_{max}$, the minimum diameter $D_{min}$, and the geometric standard deviation $\sigma_g$ in a particle diameter distribution of unagglomerated alumina particles are as shown in Table 5.

TABLE 9

| Number of Cells | l/a (x-direction) | 2000 | (—) |
|---|---|---|---|
| | m/a (y-direction) | 2000 | (—) |
| | n/a (z-direction) | 2000 | (—) |
| Unit Cell Length | a | $D_{50}/10\sigma g$ | |
| Particle Diameter Distribution | Max. Diameter Dmax | 24.5 | (μm) |
| | Min. Diameter Dmin | 9.4 | (μm) |
| | Median Diameter $D_{50}$ | 15.2 | (μm) |
| | Geom. Standard Deviation | 1.27 | (μm) |
| Dielectric Constant of Vacuum | | $8.854 \times 10^{-12}$ | (Fm$^{-1}$) |
| Dielectric Constant of Medium | | 3.78 | (—) |
| Dielectric Constant of Particles | | 9 | (—) |
| Volume Content of Particles | | 0~20 | (%) |

Figure 22:
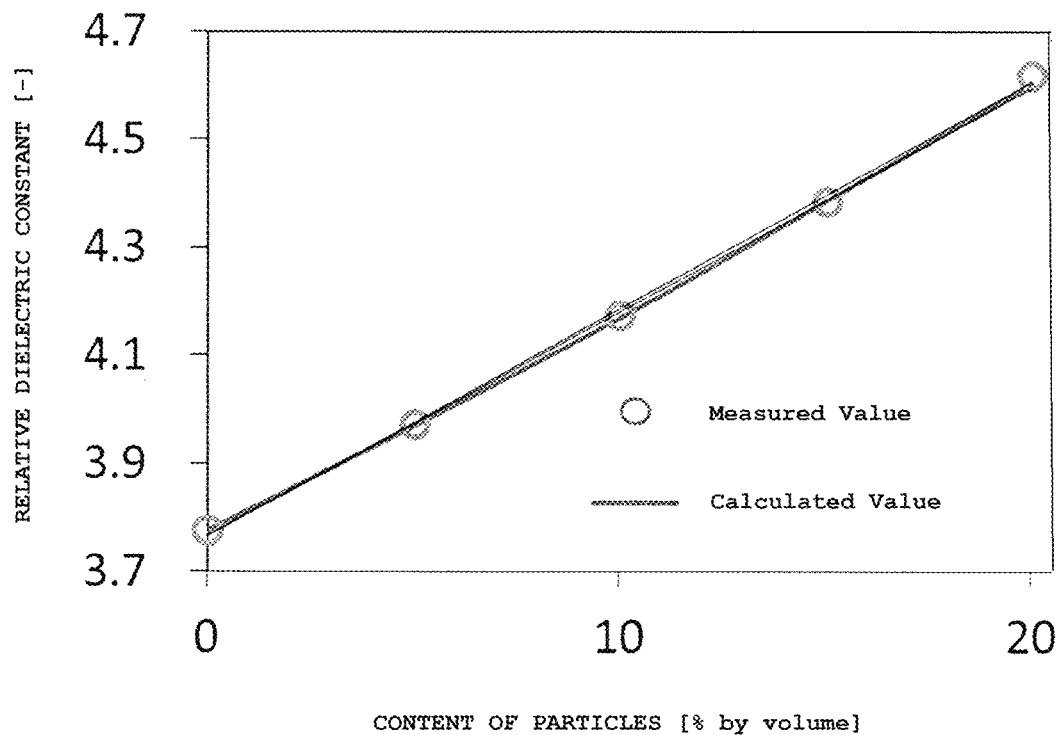
FIG. 22 is a graph showing the relation between content of particles and relative dielectric constant in Sample 6.
Figure 23:
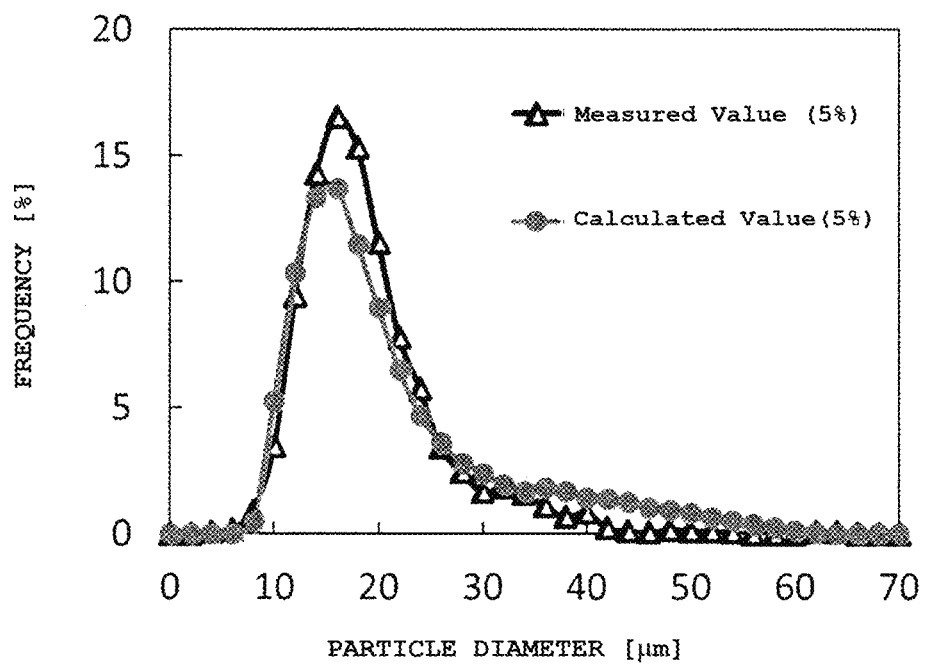
FIG. 23 is a graph showing a particle diameter distribution of measured values and a particle diameter distribution of calculated values in a particle-dispersed composite material having a content of particles of 5% by volume.
Figure 24:
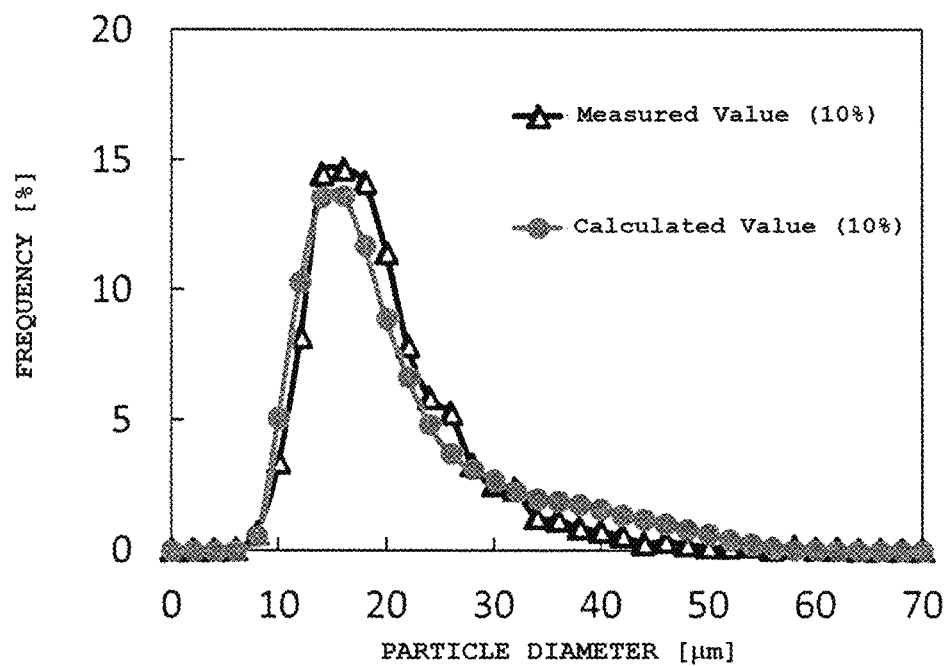
FIG. 24 is a graph showing a particle diameter distribution of measured values and a particle diameter distribution of calculated values in a particle-dispersed composite material having a content of particles of 10% by volume.
Figure 25:
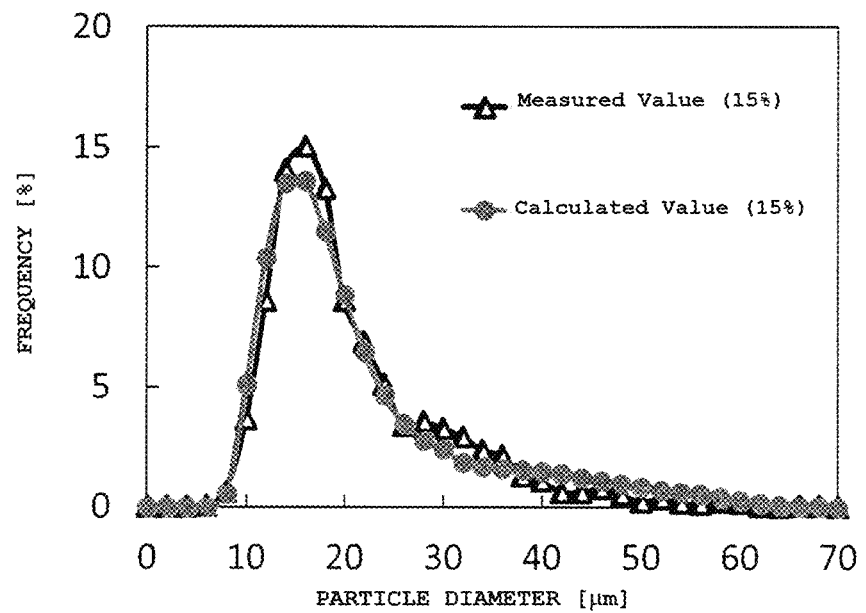
FIG. 25 is a graph showing a particle diameter distribution of measured values and a particle diameter distribution of calculated values in a particle-dispersed composite material having a content of particles of 15% by volume.
Figure 26:
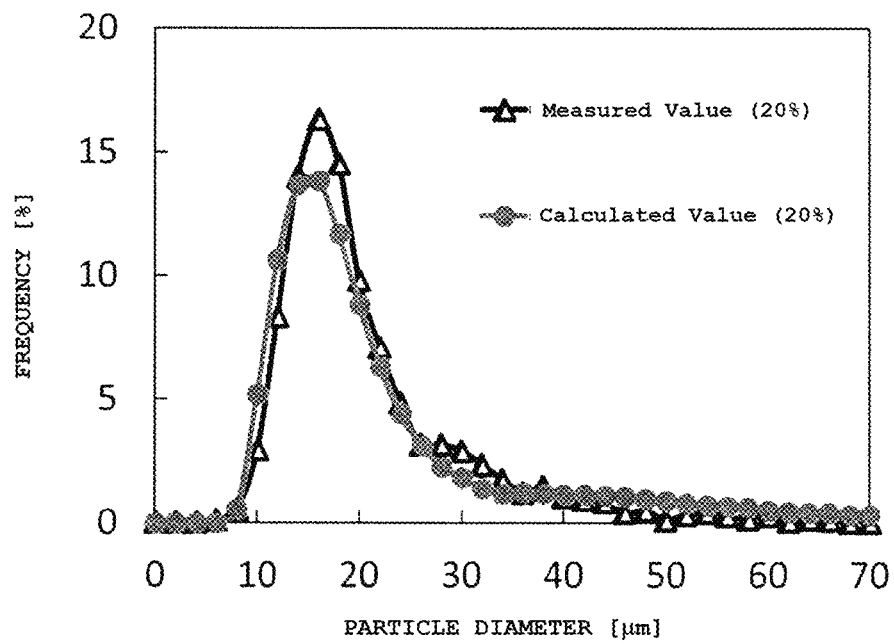
FIG. 26 is a graph showing a particle diameter distribution of measured values and a particle diameter distribution of calculated values in a particle-dispersed composite material having a content of particles of 20% by volume.

FIG. 22 is a graph showing measured values and calculated values of the relative dielectric constant of Sample 6 and shows the relation between content of particles and relative dielectric constant.

As shown in FIG. 22, the calculated values of the relative dielectric constant calculated according to the present invention are approximate to the actually measured values thereof.

As thus far described, it can be seen that the method for calculating a dielectric constant according to the present invention enables an easy calculation of a value of the relative dielectric constant close to an actual measured value.

(Evaluation of Dispersibility in Particle-Dispersed Composite Material)

In a method for evaluating dispersibility according to the present invention, arbitrary values are assumed as a volume content Va % of agglomerates in the whole of particles and an average number Na of primary particles forming the agglomerates, the relative dielectric constant $\varepsilon_{Total}$ of a cell combination is determined by the above-described method for calculating a dielectric constant according to the present invention, and values of Va and Na giving a relative dielectric constant $\varepsilon_{Total}$ nearest to the measured value of the relative dielectric constant of a particle-dispersed composite material are selected. The dispersibility is evaluated by determining from the selected values of Va and Na a particle diameter distribution of the particles inclusive of the agglomerates in the particle-dispersed composite material.

The particle-dispersed composite material in Sample 6 above was used as a sample for evaluating dispersibility. Therefore, alumina ($Al_2O_3$) particles were used as particles and polyvinyl chloride (PVC) was used as a medium.

By changing the content of alumina particles to 5% by volume, 10% by volume, 15% by volume, and 20% by volume, four types of polyvinyl chloride resin compositions containing alumina particles dispersed therein were produced. These polyvinyl chloride resin compositions were measured in terms of relative dielectric constant with an LCR meter.

Arbitrary values were assumed as a volume content Va % of agglomerates in the whole of particles and an average number Na of primary particles forming the agglomerates and simulation was performed under the conditions shown in Table 9, thus determining the respective relative dielectric constants $\varepsilon_{Total}$ of four types of cell combinations having different contents of alumina particles. This simulation was repeatedly performed and the values of Va and Na giving nearest values to the respective measured values of the relative dielectric constants of the four types of polyvinyl chloride resin compositions were selected. The selected values of Va and Na are shown in Table 10.

TABLE 10

| $Al_2O_3$ Content (% by volume) | Va (% by Volume) | Na (—) |
|---|---|---|
| 5 | 67.3 | 6.68 |
| 10 | 74.1 | 7.57 |
| 15 | 80.0 | 10 |
| 20 | 82.4 | 12 |

The particle diameter distributions in the particle-dispersed composite materials were each calculated from the values of Va and Na shown in Table 10, the number-based median particle diameter $D_{50}$, maximum diameter $D_{max}$, minimum diameter $D_{min}$, and geometric standard deviation $\sigma_g$ in the particle diameter distribution of particles in an unagglomerated state and the content of the particles in the particle-dispersed composite material. The resultant particle diameter distributions are shown as calculated values in FIGS. 23 to 26. Note that FIGS. 23, 24, 25, and 26 correspond to respective particle diameter distributions when the content of particles is 5% by volume, 10% by volume, 15% by volume, and 20% by volume, respectively.

Furthermore, the above four types of polyvinyl chloride resin compositions were measured in terms of particle diameter distribution in their actual composition using an optical microscope. The measured particle diameter distributions are shown as measured values in FIGS. 23 to 26.

As shown in FIGS. 23 to 26, the calculated values of each particle diameter distribution are very approximate to the measured values thereof, which shows that the method for evaluating dispersibility according to the present invention enables an easy and accurate evaluation of dispersibility of particles in a particle-dispersed composite material.

REFERENCE SIGNS LIST

1 . . . unit cell
10 . . . cell combination
10a . . . layer
20 . . . agglomerate
21 . . . agglomerate model

The invention claimed is:

1. A method for calculating a dielectric constant of a particle-dispersed composite material containing particles dispersed in a medium, the method comprising:
measuring a number-based median particle diameter $D_{50}$, a maximum diameter $D_{max}$, a minimum diameter $D_{min}$ and a geometric standard deviation $\sigma_g$ in a particle diameter distribution of the particles in an unagglomerated state;
assuming the particle-dispersed composite material as a cell combination in which unit cells having the same length a in each of an x-axis direction, a y-axis direction, and a z-axis direction are combined together in the x-axis direction, the y-axis direction, and the z-axis direction and which has a length l in the x-axis direction, a length m in the y-axis direction, and a length n in the z-axis direction, considering that each of the unit cells of the cell combination is constituted by a single particle element or a single medium element, and creating the cell combination in which the particle element or the medium element is assigned to each of the unit cells in consideration of the number-based median particle diameter $D_{50}$, the maximum diameter $D_{max}$, the minimum diameter $D_{min}$, and the geometric standard deviation $\sigma_g$ in the particle diameter distribution and a content of the particles in the particle-dispersed composite material; and
calculating a relative dielectric constant of the particle-dispersed composite material by assuming the cell combination as a laminate in which layers having a thickness d in the z-axis direction are combined and layered in the z-axis direction and assigning a capacitance $C_{Layer,h}$ of each of the layers represented by Formula 1 below to Formula 2 below to determine a relative dielectric constant $\varepsilon_{Total}$ of the cell combination.

$$C_{Layer,h} = \left\{ \sum_{j=1}^{\lfloor m/a \rfloor} \sum_{i=1}^{\lfloor l/a \rfloor} \left( \sum_{k=1}^{\lfloor d/a \rfloor} \frac{1}{\varepsilon_{ijk}\varepsilon_0 a} \right)^{-1} \right\}^{-1} \quad \text{Formula 1}$$

$\varepsilon_0$: dielectric constant of vacuum (F/m)

$$\varepsilon_{Total} = \frac{1}{\varepsilon_0} \cdot \frac{n}{lm} \cdot \left( \sum_{h=1}^{\lfloor n/d \rfloor} C_{Layer,h} \right)^{-1} \quad \text{Formula 2}$$

2. The method for calculating a dielectric constant of a particle-dispersed composite material according to claim 1, wherein the length a of the unit cell is $a=(D_{50}/\beta\sigma_g)$ and a fitting parameter $\beta$ is selected within a range of values where determination results of the relative dielectric constant $\varepsilon_{Total}$ have a constant standard deviation.

3. A method for evaluating dispersibility in a particle-dispersed composite material containing particles dispersed in a medium, the method comprising the steps of:
measuring a number-based median particle diameter $D_{50}$, a maximum diameter $D_{max}$, a minimum diameter $D_{min}$, and a geometric standard deviation $\sigma_g$ in a particle diameter distribution of the particles in an unagglomerated state;
measuring a relative dielectric constant of the particle-dispersed composite material to obtain a measured value of the relative dielectric constant of the particle-dispersed composite material; and
assuming arbitrary values as a volume content Va % of agglomerates in the particles and an average number Na of primary particles forming the agglomerates, determining the relative dielectric constant $\varepsilon_{Total}$ of the cell combination by the method for calculating a dielectric constant according to claim 1, and selecting values of Va and Na giving a relative dielectric constant $\varepsilon_{Total}$ nearest to the measured value of the relative dielectric constant of the particle-dispersed composite material,
wherein the dispersibility is evaluated by determining from the selected values of Va and Na a particle diameter distribution of the particles inclusive of the agglomerates in the particle-dispersed composite material.

* * * * *